(12) United States Patent
Lewis

(10) Patent No.: US 7,322,105 B2
(45) Date of Patent: Jan. 29, 2008

(54) METHODS FOR MANUFACTURING ENDODONTIC INSTRUMENTS BY MILLING

(75) Inventor: Paul Lewis, Midvale, UT (US)

(73) Assignee: Ultradent Products, Inc., South Jordan, UT (US)

( * ) Notice: Subject to any disclaimer, the term of this patent is extended or adjusted under 35 U.S.C. 154(b) by 245 days.

(21) Appl. No.: 11/282,852

(22) Filed: Nov. 18, 2005

(65) Prior Publication Data
US 2007/0116532 A1 May 24, 2007

(51) Int. Cl.
B23P 15/00 (2006.01)
B23P 15/28 (2006.01)

(52) U.S. Cl. ............. 29/896.1; 29/27 C; 409/73; 409/76; 409/213; 433/102

(58) Field of Classification Search .......... 29/896.1, 29/27 C, 27 R; 409/192, 203, 213, 217, 409/131–132, 73, 75–76, 157, 161, 165, 409/66, 72, 78; 433/102, 165, 224, 81; 76/108.1, 108.6, 115
See application file for complete search history.

(56) References Cited

U.S. PATENT DOCUMENTS

| | | | |
|---|---|---|---|
| 1,372,170 A | 3/1921 | Judd | |
| 2,173,218 A | 9/1939 | Zoppi | |
| 2,390,254 A * | 12/1945 | Henkle | 409/73 |
| 2,434,286 A | 1/1948 | Pfann | |
| 2,640,253 A * | 6/1953 | Fink et al. | 29/27 R |
| 2,701,505 A * | 2/1955 | Fink | 29/33 J |
| 2,712,775 A * | 7/1955 | Wilt, Jr. | 409/73 |
| 2,724,918 A | 11/1955 | Triman | |
| 3,803,014 A | 4/1974 | Atkinson | |
| 3,823,514 A | 7/1974 | Tsuchiya | |
| 3,869,373 A | 3/1975 | Schacher et al. | |
| 4,116,755 A | 9/1978 | Coggins et al. | |
| 4,604,884 A * | 8/1986 | Matsutani | 76/108.6 |
| 4,934,934 A | 6/1990 | Arpaio, Jr. et al. | |
| 5,382,319 A | 1/1995 | Tumminaro, Jr. | |
| 5,653,590 A | 8/1997 | Heath et al. | |
| 5,741,429 A | 4/1998 | Donadio, III et al. | |
| 5,762,497 A | 6/1998 | Heath | |
| 5,762,541 A | 6/1998 | Heath et al. | |
| 5,762,811 A | 6/1998 | Munoz | |
| 5,928,144 A | 7/1999 | Real | |
| 5,941,760 A | 8/1999 | Heath et al. | |
| 5,984,679 A | 11/1999 | Farzin-Nia et al. | |
| 6,086,773 A | 7/2000 | Dufresne et al. | |
| 6,213,771 B1 | 4/2001 | Fischer | |
| 6,315,558 B1 | 11/2001 | Farzin-Nia et al. | |

(Continued)

FOREIGN PATENT DOCUMENTS

EP    0 118 614    9/1984

(Continued)

Primary Examiner—Erica Cadugan
(74) Attorney, Agent, or Firm—Workman Nydegger

(57) ABSTRACT

A method for manufacturing endodontic instruments by milling. A provided metallic (e.g., a nickel-titanium alloy or stainless steel) thread or wire having a longitudinal axis is advanced along its longitudinal axis at a feedrate while contacting at least a portion of the metallic thread or wire with a plurality of rotating milling heads so as to remove portions of the thread or wire and yield a metallic rod including a cutting portion having a plurality of cutting edges.

21 Claims, 5 Drawing Sheets

U.S. PATENT DOCUMENTS

| | | |
|---|---|---|
| 6,575,747 B1 | 6/2003 | Riitano et al. |
| 6,702,579 B1 | 3/2004 | Hoppe et al. |
| 6,890,134 B1 | 5/2005 | Wagner et al. |
| 2006/0014480 A1 | 1/2006 | Aloise et al. |
| 2006/0185170 A1* | 8/2006 | Lewis et al. ............... 29/896.1 |

FOREIGN PATENT DOCUMENTS

| | | |
|---|---|---|
| JP | 2002144154 | 5/2002 |
| WO | WO-00/61026 A1 * | 10/2000 |

* cited by examiner

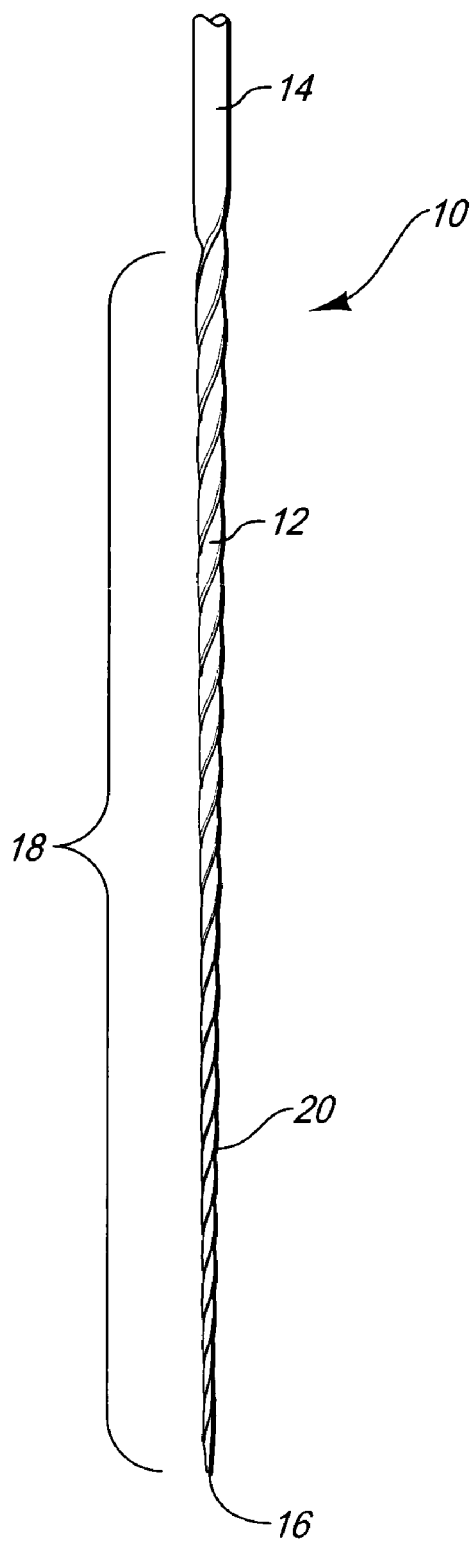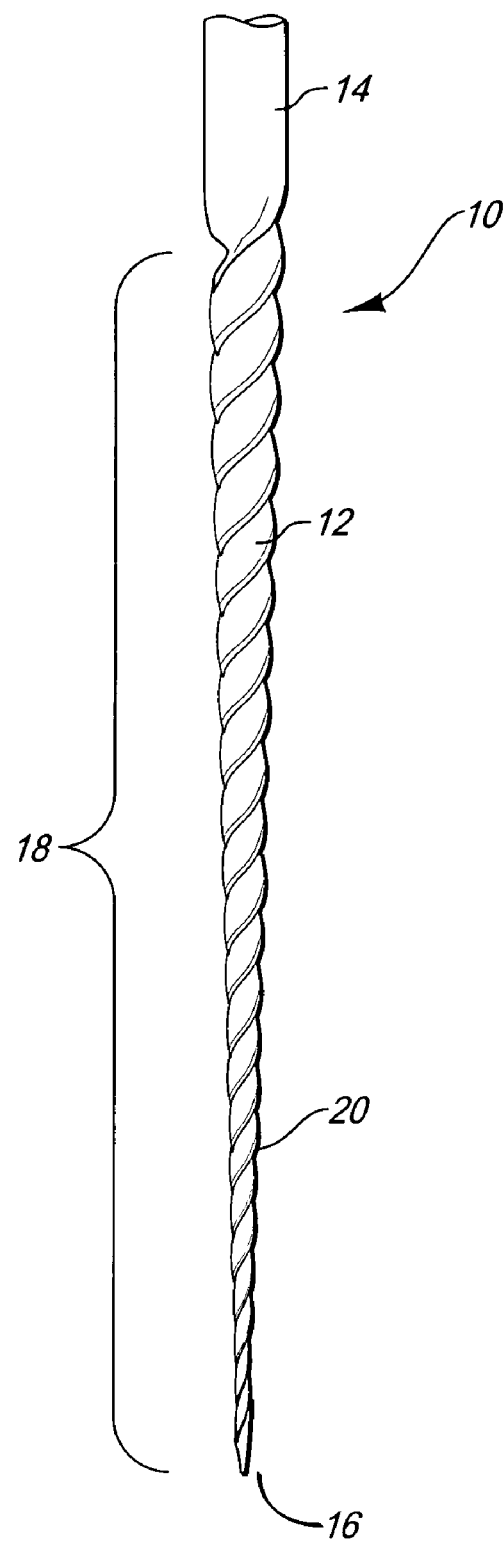
*FIG. 5A*     *FIG. 5B*

METHODS FOR MANUFACTURING ENDODONTIC INSTRUMENTS BY MILLING

BACKGROUND OF THE INVENTION

1. The Field of the Invention

The invention is in the field of endodontics and endodontic instruments for use in preparing root canals to receive a filling material such as gutta percha. More particularly, the invention is in the field of processes for manufacturing endodontic instruments.

2. The Relevant Technology

When a root canal of a living tooth becomes infected or abscessed, discomfort and, in many cases, severe pain can result. In the early days of dentistry the only solution was to pull the tooth. More recently, however, dental practitioners have learned to successfully remove the pulp material forming the nerve of the tooth that has become infected and, after careful preparation of the canal that contained the nerve material, refill the canal with an inert filling material, such as gutta percha, permitting a patient to retain the tooth.

In order to achieve a successful root canal restoration, the dental practitioner must carefully and, as completely as possible, remove the infected pulp material of the tooth to prevent continued or future infection of surrounding tissues. The removal process typically includes shaping of the root canal so that it can be effectively and successfully filled and sealed with an inert material to eliminate the possibility of further infection occurring within the cleaned and shaped root canal.

Cleaning and shaping the root canal in preparation to filling with a material such as gutta percha is achieved by the use of metal files that include cutting surfaces for removing tissue in the root canal. The cutting surfaces are typically formed by helical flutes formed in the file. One or more helical cutting surfaces may be provided, which may be axially spaced as desired.

Some existing endodontic instruments and manufacturing methods are described in U.S. Pat. No. 4,934,934, U.S. Pat. No. 5,653,590, U.S. Pat. No. 5,762,541, and U.S. Pat. No. 6,890,134.

Since root canals are seldom straight, often having bends and twists, at least some endodontic files are advantageously flexible. Currently preferred materials of construction include stainless steel, and more recently, nickel-titanium (Ni—Ti) alloys. Such materials, especially Ni—Ti alloys, exhibit good flexibility, resilience and strength, and are not likely to fail during use. Flexibility and strength are important to avoid file breakage during the cleaning process.

Endodontic instruments may be designed to be manually manipulated or to be fitted to a powered handpiece that provides rotation of the file during its use. An endodontic instrument that is intended for hand use is typically provided with an enlarged diameter plastic handle attached to the proximal end of the instrument, configured for easy manipulation between the thumb and forefinger of the dental practitioner. An instrument intended for use with a powered handpiece has a stem at the instrument proximal end configured to be removably received within a chuck of the powered handpiece, by which the instrument may then be rotated as desired by a dental practitioner.

One current method of manufacturing existing endodontic files is by a grinding operation. In the grinding operation, a metallic (typically a titanium alloy) rod is advanced past a rotating grinding wheel at a relatively slow feed rate. The depth of cut may be varied along the length of the rod in order to produce a tapered endodontic file. Such a method is disclosed in U.S. Pat. No. 5,762,541.

Tapering and grinding the rod in this way requires complex and precise machining equipment with many moving parts to perform the grinding, rotating, and tapering of the rod. The grinding apparatus can also easily become clogged with material removed from the metallic rod. The method is quite complex and relatively expensive. In addition, methods that include grinding of the rod can result in the formation of microcracks within the metal rod, which problem is particularly common when forming instruments from superelastic (e.g., Ni—Ti) metal alloy materials.

U.S. Pat. No. 6,890,134 teaches a method of manufacturing an endodontic file by use of a milling cutter tool. Although such a method may provide some advantages over grinding methods, the method as taught in U.S. Pat. No. 6,890,134 includes other disadvantages. For example, the method discloses using a single milling cutter tool to cut material from a metallic blank, forming a single helical flute into the metallic blank. It is often desired to manufacture endodontic instruments including multiple flutes, which would require refeeding of the metallic rod through the milling apparatus two or more times. In addition to the increased manufacturing time and cost, it can be very difficult to achieve high quality and precision in the cutting of additional helical flutes when refeeding of the metallic rod is required. The result may be increased rejection rates for manufactured parts and increased costs.

It would be an improvement in the art to provide an alternative method of manufacture capable of producing tapered endodontic instruments having multiple helical flutes at a reasonable cost.

BRIEF SUMMARY OF THE INVENTION

The present invention provides a method for manufacturing endodontic instruments. According to one embodiment, the invention involves the steps of (a) providing a metallic (e.g., a nickel-titanium alloy) thread or wire blank having a longitudinal axis; and (b) advancing the metallic thread or wire along its longitudinal axis at a feedrate while simultaneously contacting at least a portion of the metallic thread or wire with a plurality of rotating milling heads such that the milling heads remove a portion of the wire blank, yielding a milled metallic rod including a cutting portion having a plurality of cutting edges.

In one example, the metallic thread or wire is rotated about its longitudinal axis during the procedure, resulting in a metallic rod having a plurality of helical flutes formed therein. The number of formed flutes corresponds to the number of milling heads. In other words, each milling head forms a single flute during a single pass of the metallic wire or thread such that multiple flutes are formed simultaneously. This manufacturing method allows formation of multiple helical flutes in the metallic wire in a single pass through the manufacturing apparatus.

In another example, the metallic wire or thread may initially include a substantially circular cross section so as to be cylindrical in shape, but the initially, cylindrical metallic wire or thread is not rotated during the shaping process. The wire or thread may be shaped by the plurality of rotating milling heads so as to yield an intermediate metallic rod having any of various polygonal cross sections, such as triangular, square, or any of various regular or irregular shapes bounded by straight or curved sides. At least a portion of the metallic rod is later torsioned, which may be accomplished by holding one end of the cutting portion stationary while twisting the opposite end. Torsioning the rod causes the apices of the polygon to be twisted to form helical cutting surfaces along the cutting portion of the rod. In other words, the helical configuration of the cutting edges may be accomplished either by rotating the metallic wire during milling or by later torsioning the metallic wire so as to cause the cutting edges to assume a helical configuration.

The formed cutting portion may be tapered. For example, this may be accomplished by adjusting the position of the milling heads relative to the metallic wire or thread during the milling process (i.e., progressively pulling out and/or pushing in the milling heads relative to the wire or thread being milled).

In one example, the milling heads may be located in a single plane, or alternatively they may be configured such that at least one of the milling heads is located in a plane different from at least one other milling head.

The milling heads may include a rounded ball head or a substantially flat head at the working end. Different shaped ends may affect the cross sectional configuration of the finished endodontic instrument formed from the metallic wire blank. In addition, either the head working end or the sides of the milling heads may contact the metallic wire or thread during shaping. For example, when shaping a cylindrical metallic thread or wire so as to have a polygonal (e.g., triangular or rectangular) cross section, it may be desirable to contact the metallic thread or wire with the side of each milling head, using the side of the milling head to cut material from the wire blank. Such a process can be used to shave off the perimeter of a cylindrical wire blank to create a metallic rod having a polygonal cross section (e.g., triangular or rectangular). The metallic rod may then be torsioned to create a cutting portion with a plurality of helical cutting edges.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 5A and 5B depict exemplary tapered metallic rods including a plurality of cutting edges.

DETAILED DESCRIPTION OF THE PREFERRED EMBODIMENTS

A detailed description of the invention endodontic instruments and manufacturing methods will now be provided, with specific reference to figures illustrating preferred embodiments of the invention. It will be appreciated that like structures will be provided with like reference designations. To provide context for interpreting the scope of the invention, certain terms used throughout the application will now be defined.

As used herein, the terms endodontic "instrument" and endodontic "instruments" refer to endodontic files and other instruments used in a root canal or other endodontic procedure.

As used herein, the terms "polygon" and "polygonal" refer to a shape that is closed and bounded by straight or curved sides. Non-limiting examples include a triangle, a square, a rectangle, a pentagon, a spherical triangle, or any other of various regular or irregular shapes, including, but not limited to, the shapes disclosed herein, as exemplified in FIGS. 3A-3G.

As used herein, the terms "milling" and "turning" refer to a procedure whereby a metallic material is cut or shaped by contact with a plurality of rotating milling heads. While contacted by the rotating milling heads, the shaping occurs as bits of material are "milled" or "cut" away because of the action of the milling heads.

I. Exemplary Endodontic Instruments

Figure 1:
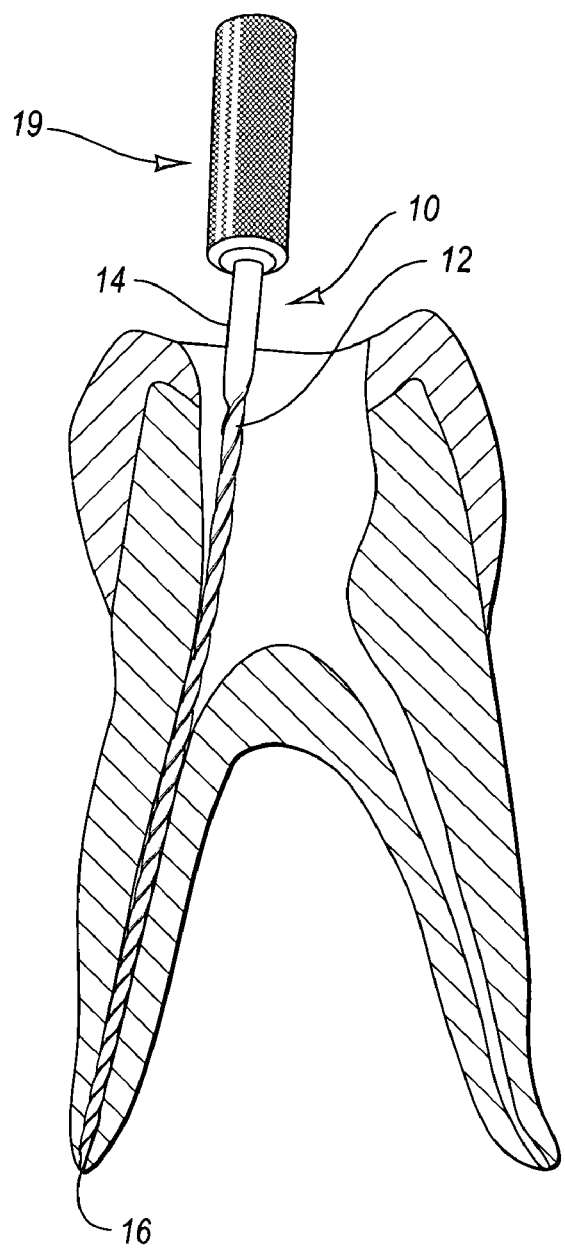
FIG. 1 is a cross sectional view of a tooth having two roots, with an endodontic instrument being positioned in one of the roots.
Figure 2:
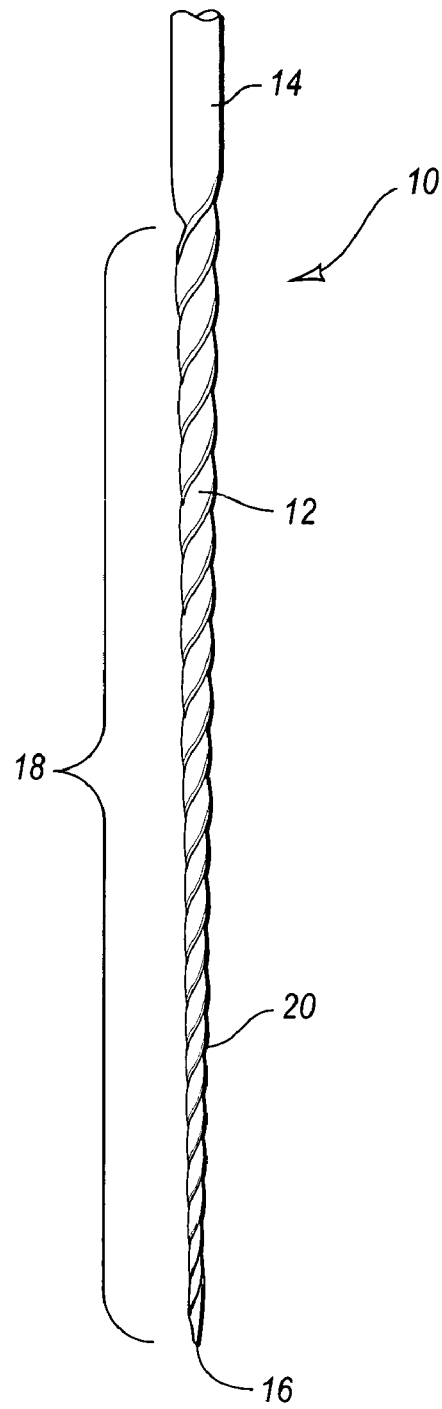
FIG. 2 is a perspective view of the cutting portion of an exemplary endodontic instrument.

Referring to FIGS. 1 and 2, an endodontic instrument 10 is illustrated which comprises a metallic rod 12 having a proximal end 14, and a distal end 16. At least a portion of the metallic rod 12 comprises a cutting portion 18 of the endodontic instrument, which is disposed between the proximal end 14 and the distal end 16. In this embodiment, the cutting portion 18 includes a plurality of helical cutting edges 20 that extend helically around metallic rod 12. A handle 19 may be provided adjacent the proximal end 14 of the metallic rod 12 in order to facilitate gripping of the endodontic instrument 10 by the user or a dental hand piece (e.g., a reciprocating hand piece).

The cutting portion 18 is preferably tapered between the proximal end 14 and the distal end 16, with decreasing diameter or width toward the distal end 16. The taper may be continuous or incremental (i.e., stair stepped). The taper may be any amount desired, but is preferably between about 0.02 mm/mm and about 0.06 mm/mm. The specific taper of any instrument will depend on the intended use and dental practitioner preference. For example, a taper of 0.0225 mm/mm may be preferred when preparing a root canal that is to receive a gutta percha cone having a taper of about 0.02 mm/mm.

The cutting portion 18 may have a length of about 2 mm up to the full length of the rod 12, which may be as much as about 30 mm or more. In the illustrated embodiment, the cutting portion 18 has a length sufficient to extend substantially the full depth of a tooth root canal as illustrated in FIG. 1. It will be appreciated, however, that the cutting portion may terminate before reaching the tip 16, as in a coronal file, or comprise a small length near the tip 16 as in an apical file.

Figure 3A:
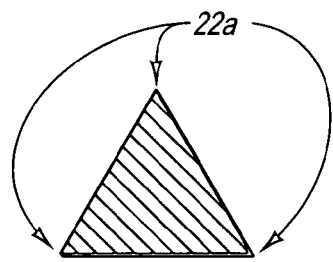
FIGS. 3A-3G illustrate several different polygonal transverse cross sections through several exemplary endodontic instruments manufactured according to the method of the present invention.

The cross sectional configuration of the cutting portion 18 of the instrument illustrated in FIGS. 1 and 2 is triangular and is composed of three linear sides, as best seen in FIG. 3A. The apices 22*a* of the triangle form cutting edges 20. The cutting portion 18 may be of any polygonal cross section (e.g., those illustrated in FIGS. 3A-3G).

Figure 3B:
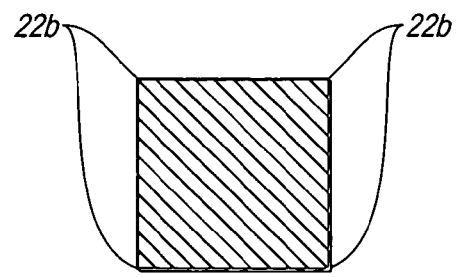
Figure 3C:
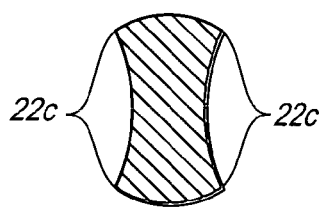

Several non-limiting examples of suitable polygonal cross sections are illustrated in FIGS. 3A-3G. FIG. 3A illustrates a triangular cross section in which apices 22a form three cutting edges 20. FIG. 3B illustrates a square cross section in which line intersections 22b form four cutting edges. FIG. 3C illustrates a cross section bounded by four curved sides, two of which are concave and two of which are convex. The intersections 22c between the convex and concave sides form four cutting edges.

Figure 3D:
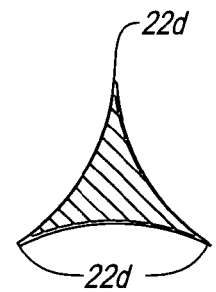
Figure 3E:
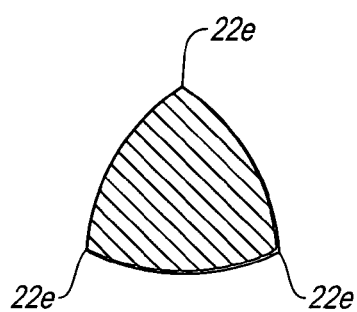

FIGS. 3D and 3E illustrate alternative spherical triangular cross sections, with the triangle cross section of FIG. 3D having concave surfaces between the apices 22d of the triangle and with the triangle cross section of FIG. 3E having convex surfaces between apices 22e of the triangle.

Figure 3F:
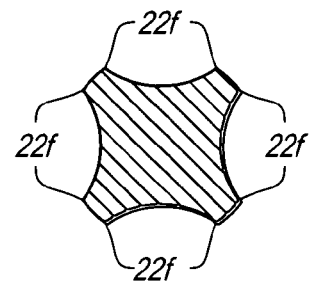
Figure 3G:
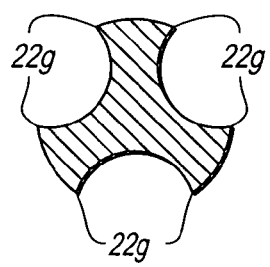

FIG. 3F illustrates a cross section bounded by a combination of four concavely curved sides separated by four convexly curved sides. The intersections 22f between the convexly and concavely curved sides form eight cutting edges. FIG. 3G illustrates a cross section of an irregular polygon bounded by three concavely curved sides separated by three convexly curved sides. The intersections 22g between the six curved sides yield six cutting surfaces.

II. Method of Manufacture

FIGS. 4A-4D illustrate an exemplary apparatus for manufacturing endodontic instruments according to the present inventive method. As will be further described below, the method involves a process which has been found to efficiently produce endodontic instruments of the type described, from a metallic wire blank. The metallic wire may be formed of any suitable metallic material, for example stainless steel, a nickel-titanium alloy (Ni—Ti), nickel-titanium-chromium alloy, a nickel-titanium-copper alloy, a nickel-titanium-niobium alloy, or another superelastic metallic material. One titanium superelastic metallic material known as "gum metal" is available from Toyota in Japan. Additional details regarding the formation and properties of "gum metal" are described in U.S. patent application Ser. No. 11/176,839, filed on Jul. 7, 2005 and entitled "DENTAL INSTRUMENTS MADE FROM SUPERELASTIC ALLOYS," which is incorporated herein by reference.

Nickel-titanium alloys are one preferred elastic material because they are strong, yet flexible and resilient. The Ni—Ti alloy preferably has a titanium content in a range of about 20% to about 80%, more preferably in a range of about 30% to about 70%, and most preferably in a range of about 40% to about 60%. In one embodiment, the balance of the alloy may comprise nickel and small amounts of other ingredients which do not adversely affect the suitability of the material for use as an endodontic instrument.

The wire blank from which the endodontic instrument is to be manufactured may be supplied in a circular cross section and then shaped according to the method of the present invention. With regard to wire thickness, endodontic instruments are sized in accordance with established standards, which range from a thickness at the distal end 16 of 1.4 mm (size 140) to a thickness at the distal end 16 of 0.06 mm (size 06).

Figure 4A:
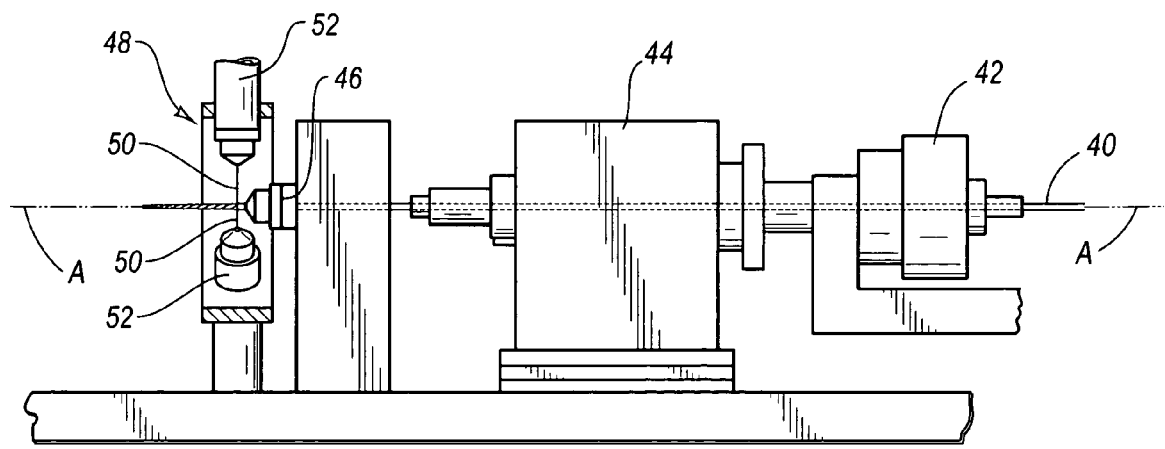
FIGS. 4A-4D depict an exemplary machining apparatus including a plurality of rotatable milling heads used to form a plurality of cutting edges into a metallic wire blank.
Figure 4B:
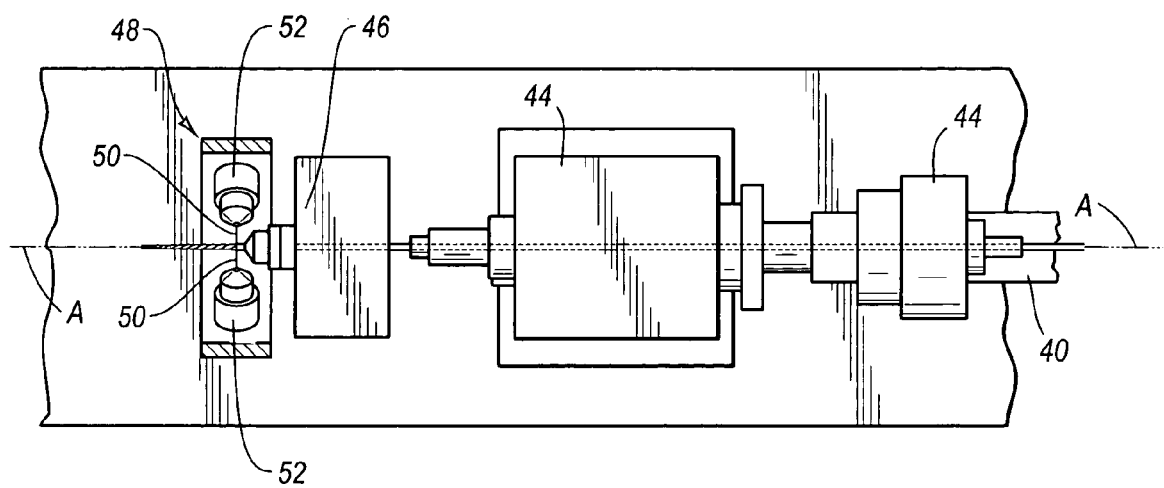
Figure 4C:
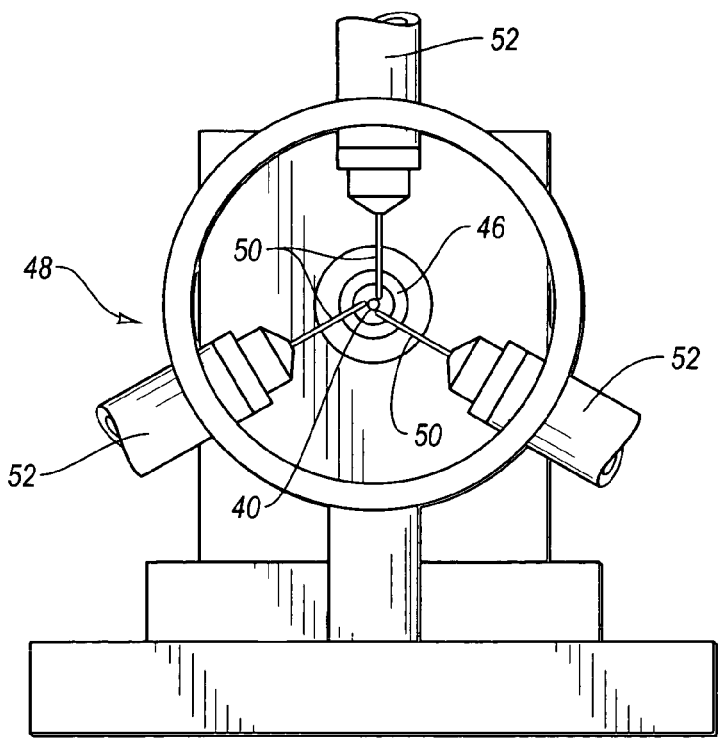

FIGS. 4A and 4B depict a side view and a top view respectively of an apparatus for as forming a cutting edge or surface into a metallic wire. The apparatus may also simultaneously produce a desired taper of the cutting portion of the formed endodontic instrument. A metallic thread or wire 40 having a longitudinal axis A, which wire may be continuous, is positioned so as to extend through an axial feed block 42 and an indexing block 44 of conventional construction. A work-holding fixture 46 is positioned to support the forward end of the wire 40 adjacent to milling head assembly 48, which includes multiple milling heads 50. Each milling head 50 may be held within a chuck 52, with each chuck being attached to milling head assembly 48. The milling heads 50 are shown in the figures as shank-type endmilling tools. In the side view and top view of FIGS. 4A-4B, two milling heads 50 are shown so as to more clearly show the overall apparatus, although typically three milling heads may be present (e.g., three milling heads 50 each spaced about 120° apart). FIG. 4C illustrates an end view showing three milling heads 50, each positioned about 120° apart. Although illustrated with three milling heads, it is to be understood that only two milling heads may be used (e.g., two milling heads each spaced about 180° apart), or more than three milling heads may be used. In one example, the milling heads may be evenly spaced (e.g., 180° apart for 2 heads, 120° apart for 3 heads, 90° apart for 4 heads, etc.).

The two blocks 42 and 44 may be advanced along longitudinal axis A so that the wire 40 is axially moved through milling head assembly 48 at a relatively slow feed rate (e.g., between about 3-8 inches per minute). Rotating milling heads 50 contact wire 40, cutting flutes into the length of wire 40 as wire 40 is advanced along axis A. Concurrently with the axial movement of wire 40, the indexing block 44 may serve to slowly rotate the wire 40 about axis A at a controlled speed. Rotating wire 40 while milling heads 50 cut flutes into wire 40 causes the milled surface of wire 40 to assume a helical configuration. For example, an embodiment as illustrated in FIG. 4C where the milling heads 50 are spaced about 120° apart may result in a cross section as illustrated in FIG. 3D or FIG. 3G depending on the diameter of milling heads 50 relative to wire 40. In FIG. 4C milling heads 50 include a rounded ball tip at the milling end and are oriented eccentrically relative to wire 40 such that the relatively stationary center of rotating milling heads 50 are not used to form the final milled surface in wire 40. Such an eccentric alignment minimizes or prevents the creation and propagation of micro-fractures that may otherwise form within wire 40.

The wire 40 preferably moves through the milling assembly 48 only once, such that all of the cutting edges and flutes are formed in a single pass. Shaping wire 40 with multiple milling heads 50 simultaneously allows all cutting edges to be formed in a single pass, rather than requiring wire 40 to be fed through a second or third time (or more) to form additional flutes. For example, a wire 40 having an initially round cross section may be shaped by two milling cutters 50 that contact wire 40 so as to mill two flutes into wire 40, resulting in a cross section having four cutting edges as illustrated in FIG. 3C. Three milling cutters 50 may be used so as to shape three flutes (e.g., the embodiments of FIGS. 3D and 3G). Four milling cutters 50 may be used to shape four flutes (e.g., the embodiment of FIG. 3F). The milling heads may remove as much or as little material as needed to form any desired cross section. Cross sections in addition to those illustrated in FIGS. 3A-3G will be apparent to those skilled in the art.

The rotating milling heads 50 are preferably rotated at a relatively high speed of between about 5,000 RPM and about 10,000 RPM. A high rotation speed may be preferred so as to decrease the amount of time required to produce each endodontic instrument, although lower rotation speeds (e.g., less than about 5,000 RPM) are within the scope of the inventive method. The milling heads 50 may be oriented to rotate about an axis generally perpendicular to the axis of the advancing wire 40, as illustrated in FIGS. 4A-4B. Alternatively, the milling heads 50 may be angled relative to advancing wire 40.

If the instrument is to have a tapered cutting portion, the milling heads 50 may be progressively moved slightly toward or away from wire 40 during the milling process so as to form a cutting portion having a tapered configuration. This progressive movement of milling heads 50 may be incremental or continuous. Incremental movement results in a non-continuous, stair-step like taper, while continuous movement results in a continuous smooth taper.

Figure 4D:
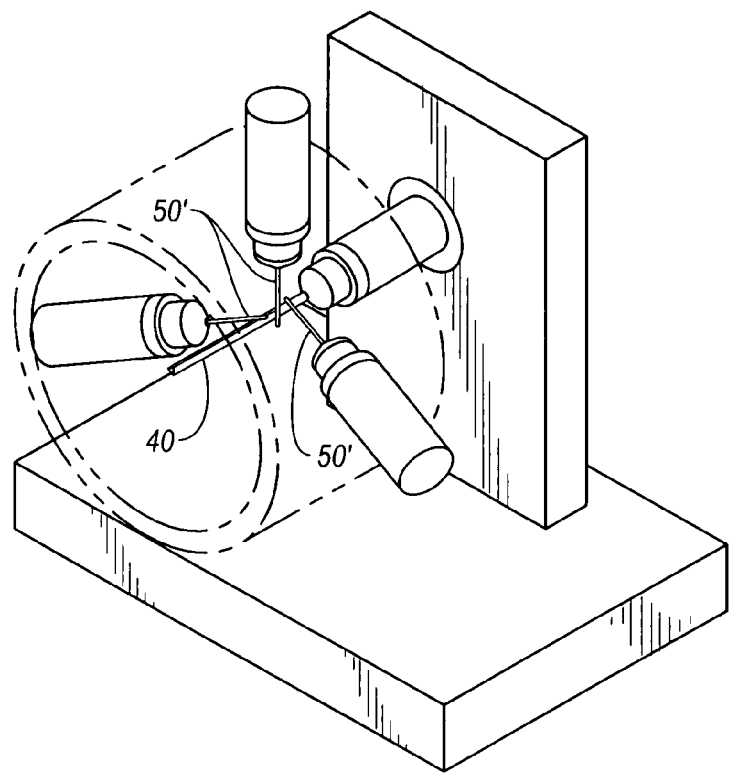
Figure 4A:
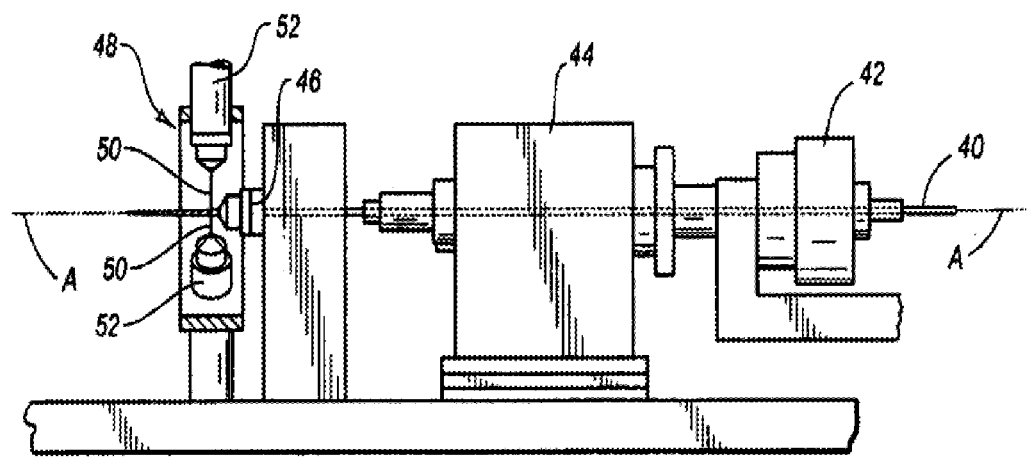
Figure 4B:
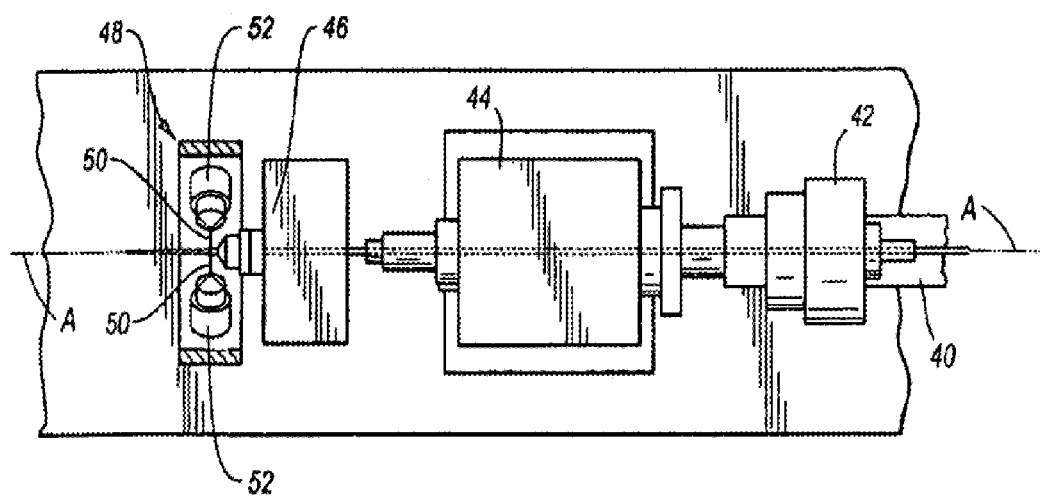

In an alternative method illustrated in FIG. 4D, the wire 40 may be held rotatably stationary such that it does not rotate about axis A. Rotating milling heads 50' may be oriented with respect to wire 40 such that wire 40 is contacted by the sides of milling head 50' (as opposed to the ends of the milling heads). In the illustrated configuration, an initially round cross section of wire 40 may be shaped by milling heads 50' by removing portions of the perimeter of wire 40 so as to mill the initially circular cross section into a desired cross section of a different shape. For example, three milling heads 50 may be used to shape a triangular cross section (e.g., FIG. 3A). Four milling heads may be used to shape a rectangular or square cross section (e.g., FIG. 3B). In one example, the milling heads may be evenly spaced apart (e.g., 120° apart for 3 heads, 90° apart for 4 heads, 72° apart for 5 heads). Examples of additional cross sections that may be milled by this method will be apparent to one skilled in the art.

In addition, the milling heads 50' may be located in the same plane (as illustrated in FIGS. 4A-4C), or different planes, as illustrated in FIG. 4D. Such an embodiment may be particularly desirable when using a side of milling head 50', rather than the end, to contact and mill wire 40. The end of any of milling heads 50 or 50' may be rounded or flat, as desired.

In embodiments where the wire 40 is not rotated during the shaping process, once a polygonal cross section (e.g., those illustrated in FIGS. 3A-3G) has been formed, the cutting portion may be torsioned so as to produce a helical configuration of the cutting edges along the cutting portion. Further details of torsioning the cutting portion are disclosed in U.S. patent application Ser. No. 10/991,178 filed Nov. 17, 2004 and titled METHODS FOR MANUFACTURING ENDODONTIC INSTRUMENTS, hereby incorporated by reference.

In an alternative embodiment, a polygonal cross section (e.g., those illustrated in FIGS. 3A-3G or even round) may be formed (e.g., including a taper), after which the blank may be cold formed to complete the formation of cutting edges within the blank (e.g., by passing the tapered blank between two or more dies comprising a negative impression that corresponds to the cutting edges of the endodontic instrument). Exemplary cold forming processes are described in U.S. patent application Ser. No. 11/063,354, filed Feb. 23, 2005, and entitled METHODS FOR MANUFACTURING ENDODONTIC INSTRUMENTS and U.S. patent application Ser. No. 11/063,757, filed Feb. 23, 2005, and entitled METHODS FOR MANUFACTURING ENDODONTIC INSTRUMENTS FROM POWDERED METALS, both of which are herein incorporated by reference.

An alternative chemical milling process for tapering the metallic rod (e.g., if the polygonal cross section formed as described above is not initially tapered) is described in U.S. patent application Ser. No. 10/436,938, filed May 13, 2003 now U.S. Pat. No. 6,968,619, and entitled METHODS FOR MANUFACTURING ENDODONTIC INSTRUMENTS, and U.S. patent application Ser. No. 10/991,178, filed Nov. 17, 2004, and entitled METHODS FOR MANUFACTURING ENDODONTIC INSTRUMENTS, both of which are herein incorporated by reference.

Using a plurality of milling heads 50 to form a desired cross section including a number of cutting edges allows for multiple cuts to be performed simultaneously. Such a method and configuration may eliminate the need to run wire 40 through the cutting operation more than once. For example, methods using only a single milling head are able to form only a single flute or make a single cut within wire 40 for each pass. When forming an endodontic instrument requiring more than a single flute or cut (e.g., any of the cross sections illustrated in FIGS. 3A-3G), the wire 40 must be re-fed through the apparatus one or more additional times in order to form additional flutes or make additional cuts. Re-feeding requires precise positioning and control to accurately align each subsequent cut with the preceding cut or cuts, which can be extremely difficult, particularly when working with wire diameters that are very small, as endodontic instruments are. In addition, any gripping by the apparatus necessary to re-feed the wire may distort or otherwise crush the delicate sharp cutting edges that have previously been formed.

The result is increased rates of rejection, increased cost, and increased time required to manufacture instruments by such a method. The present inventive method allows two, three, or more flutes or cuts to be made simultaneously in a single pass. In addition to being more efficient, cutting portions of endodontic instruments formed by such a method are of a higher quality, exhibiting less variability, more consistency, and better accuracy as a result of forming all of the flutes or cuts simultaneously.

In an alternative but less preferred embodiment, the wire may be re-fed for milling of additional cuts or flutes, but because multiple milling heads are used, the number of times the wire must be refed will be less than with other methods that use only a single milling head. For example, four cuts or flutes may be made by passing a wire through an apparatus including two milling heads with two passes (versus four passes required when making such an instrument by use of a single milling head). Six cuts may be made by passing a wire through an apparatus including three milling heads with two passes (versus six passes required when making such an instrument by use of a single milling head. The use of multiple milling heads substantially reduces the number of required passes through the milling apparatus.

Once a cutting portion has been milled into wire 40, the wire 40 may then be severed by conventional techniques, such as by axially advancing the rod 40 and then moving one of the milling heads 50 through the wire 40, or through use of a cutting blade fixed to the apparatus (not shown).

FIGS. 5A-5B illustrate exemplary endodontic instruments 10 having continuous tapered cutting portions 18. The instrument illustrated in FIG. 5A includes a taper of about 0.02 mm/mm while that illustrated in FIG. 5B includes a taper of about 0.06 mm/mm.

After milling, the rod 12 is then further processed in a conventional manner to form the completed instrument as illustrated for example in FIG. 1 (e.g., fitting a handle or stem 19 to proximal end 14, optionally, surface finishing the rod 12, etc). The process as described and claimed has been found to produce inexpensive high quality endodontic instruments.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A method of manufacturing an endodontic instrument for use in performing an endodontic procedure, comprising:
    (a) providing a metallic thread or wire having a longitudinal axis; and
    (b) advancing the metallic thread or wire along the longitudinal axis at a feedrate while contacting at least a portion of the metallic thread or wire with a plurality of rotating shank-type endmilling tools that are peripherally spaced about the longitudinal axis of the thread or wire so as to remove a portion of material from the thread or wire.

2. A method as recited in claim 1, wherein (b) yields a metallic rod including a cutting portion having a plurality of cutting edges.

3. A method as recited in claim 1, further comprising rotating the metallic thread or wire about the longitudinal axis simultaneous with (b).

4. A method as recited in claim 3, wherein the plurality of endmilling tools simultaneously contacts at least a portion of the metallic thread or wire so as to simultaneously form a plurality of helical flutes within the metallic thread or wire.

5. A method as recited in claim 1, wherein the metallic thread or wire is initially cylindrical in shape.

6. A method as recited in claim 5, wherein at least a portion of the initially cylindrical metallic thread or wire is shaped by the plurality of endmilling tools so as to yield an intermediate metallic rod having a polygonal cross section.

7. A method as recited in claim 6, wherein the polygonal cross section is at least one of a square, a triangle, a polygon having straight surfaces, a polygon having concave surfaces, or a polygon having convex surfaces.

8. A method as recited in claim 6, further comprising torsioning the intermediate metallic rod having a polygonal cross section so as to form helical cutting edges in a cutting portion of the instrument.

9. A method as recited in claim 1, wherein (b) produces a cutting portion that is tapered.

10. A method as recited in claim 9, wherein the taper is between about 0.02 mm/mm and about 0.06 mm/mm.

11. A method as recited in claim 1, wherein the plurality of endmilling tools are located in a single plane.

12. A method as recited in claim 1, wherein at least one of the endmilling tools is located in a plane different from at least one other endmilling tool.

13. A method as recited in claim 1, wherein at least one of the endmilling tools comprises a rounded ball head end.

14. A method as recited in claim 1, wherein at least one of the endmilling tools comprises a substantially flat head end.

15. A method as recited in claim 1, wherein the metallic thread or wire is contacted and milled by an end of at least one of the endmilling tools.

16. A method as recited in claim 1, wherein the metallic thread or wire is contacted and milled by a side of at least one of the endmilling tools.

17. A method as recited in claim 1, further comprising cold forming the metallic thread or wire to yield a metallic rod including a cutting portion having a plurality of cutting edges.

18. A method of manufacturing an endodontic instrument for use in performing an endodontic procedure, comprising:
    (a) providing a metallic thread or wire having a longitudinal axis;
    (b) advancing the metallic thread or wire along the longitudinal axis at a feedrate while contacting at least a portion of the metallic thread or wire with a plurality of rotating shank-type endmilling tools so as to remove a portion of material from the metallic thread or wire; and
    (c) rotating the metallic thread or wire about the longitudinal axis simultaneous with (b) so as to form a plurality of helical flutes within the metallic thread or wire.

19. A method as recited in claim 18, wherein (b) includes contacting at least a portion of the metallic thread or wire with at least three rotating shank-type endmilling tools so as to form at least three helical flutes in (c).

20. A method of manufacturing an endodontic instrument for use in performing an endodontic procedure, comprising:
    (a) providing a metallic thread or wire having a longitudinal axis;
    (b) advancing the metallic thread or wire along the longitudinal axis at a feedrate while contacting at least a portion of the metallic thread or wire with a plurality of rotating shank-type endmilling tools that are peripherally spaced about the longitudinal axis so as to remove a portion of material from the wire, wherein at least a portion of the metallic thread or wire is shaped by the plurality of rotating shank-type milling tools so as to yield an intermediate metallic rod having a polygonal cross section; and
    (c) torsioning the intermediate metallic rod having a polygonal cross section so as to form helical cutting edges in a cutting portion of the instrument.

21. A method as recited in claim 20, wherein the polygonal cross section is at least one of a square, a triangle, a polygon having straight surfaces, a polygon having concave surfaces, or a polygon having convex surfaces.

* * * * *

UNITED STATES PATENT AND TRADEMARK OFFICE
CERTIFICATE OF CORRECTION

PATENT NO. : 7,322,105 B2
APPLICATION NO. : 11/282852
DATED : January 29, 2008
INVENTOR(S) : Paul Lewis It is certified that error appears in the above-identified patent and that said Letters Patent is hereby corrected as shown below:

<u>Drawings</u>
Delete drawing Sheet 3 of 5 and substitute therefor the drawing sheet consisting of FIG 4A - 4B as shown on the attached pages <u>Column 4</u>
Line 4, change "invention" to --inventive--

<u>Column 10</u>
Line 26, change "simultaneous" to --simultaneously--

Signed and Sealed this

Thirtieth Day of September, 2008

JON W. DUDAS
*Director of the United States Patent and Trademark Office*